US012575802B2

(12) United States Patent
Kim et al.

(10) Patent No.: US 12,575,802 B2
(45) Date of Patent: Mar. 17, 2026

(54) METHOD AND ELECTRONIC DEVICE FOR CLASSIFYING VESSEL

(71) Applicant: Medipixel, Inc., Seoul (KR)

(72) Inventors: Hyun-Woo Kim, Seoul (KR); Sooncheol Noh, Seoul (KR); Yeong Heon Mok, Seoul (KR)

(73) Assignee: Medipixel, Inc., Seoul (KR)

( * ) Notice: Subject to any disclaimer, the term of this patent is extended or adjusted under 35 U.S.C. 154(b) by 0 days.

(21) Appl. No.: 18/975,499

(22) Filed: Dec. 10, 2024

(65) Prior Publication Data

US 2025/0186012 A1 Jun. 12, 2025

(51) Int. Cl.
*A61B 6/50* (2024.01)
*A61B 6/00* (2024.01)

(52) U.S. Cl.
CPC .............. *A61B 6/504* (2013.01); *A61B 6/547* (2013.01)

(58) Field of Classification Search
None
See application file for complete search history.

(56) References Cited

U.S. PATENT DOCUMENTS

| | | | | |
|---|---|---|---|---|
| 6,324,254 B1 * | 11/2001 | Pflaum | ............... | A61B 6/466 |
| | | | | 378/95 |
| 2020/0310471 A1 * | 10/2020 | Hogg | ............... | A61B 5/065 |
| 2021/0012901 A1 | 1/2021 | Hsieh et al. | | |
| 2022/0084658 A1 * | 3/2022 | Hooker | ............... | G06T 7/70 |
| 2022/0167912 A1 * | 6/2022 | Lyu | ............... | G06T 7/149 |
| 2022/0301162 A1 | 9/2022 | Kweon et al. | | |
| 2024/0050059 A1 | 2/2024 | Shin et al. | | |
| 2024/0273723 A1 * | 8/2024 | Tison | ............... | A61B 8/0891 |

FOREIGN PATENT DOCUMENTS

| | | |
|---|---|---|
| CN | 114469153 A | 5/2022 |
| KR | 10-2021-0101639 A | 8/2021 |
| KR | 10-2022-0092433 A | 7/2022 |
| WO | WO-2021246648 A1 * | 12/2021 ............. A61B 6/467 |
| WO | 2023152688 A1 | 8/2023 |

OTHER PUBLICATIONS

Apr. 1, 2025—(EP) Extended European Search Report—App. 24218950.4.

* cited by examiner

*Primary Examiner* — Patricia J Park
(74) *Attorney, Agent, or Firm* — Banner & Witcoff, Ltd.

(57) ABSTRACT

A method of classifying vessels, performed by at least one processor, the method including: acquiring an image including the cardiovascular vessels of a subject and angle information of an image acquisition device for the subject; and based on the angle information, identifying at least one type of cardiovascular vessel included in the image is disclosed.

18 Claims, 11 Drawing Sheets

| β \ α | RAO | | AP | | LAO | |
|---|---|---|---|---|---|---|
| | VESSEL TYPE | IDENTIFICATION LEVEL | VESSEL TYPE | IDENTIFICATION LEVEL | VESSEL TYPE | IDENTIFICATION LEVEL |
| CRA | LM | | LM | | LM | + |
| | LAD-p | + | LAD-p | + | LAD-p | + |
| | LAD-m | ++ | LAD-m | + | LAD-m | + |
| | LAD-d | ++ | LAD-d | + | LAD-d | + |
| | LCX-p | - | LCX-p | - | LCX-p | - |
| | LCX-d | - | LCX-d | - | LCX-d | - |
| (-) | | | | | | |
| | | | LAD | + | | |
| | | | | | | |
| | | | | | | |
| | | | | | | |
| | | | | | | |
| CAU | LM | + | LM | ++ | LM | ++ |
| | LAD-p | + | LAD-p | + | LAD-p | + |
| | LAD-m | - | LAD-m | - | LAD-m | - |
| | LAD-d | - | LAD-d | - | LAD-d | - |
| | LCX-p | + | LCX-p | + | LCX-p | + |
| | LCX-d | + | LCX-d | + | LCX-d | - |

FIG. 6

| α / β | RAO | | AP | | LAO | |
|---|---|---|---|---|---|---|
| | VESSEL TYPE | IDENTIFICATION LEVEL | VESSEL TYPE | IDENTIFICATION LEVEL | VESSEL TYPE | IDENTIFICATION LEVEL |
| CRA | prox. | ++ | prox. | | prox. | ++ |
| | mid. | + | mid. | + | mid. | + |
| | dis. | | dis. | ++ | dis. | + |
| (–) | prox. | – | prox. | | prox. | + |
| | mid. | ++ | mid. | | mid. | + |
| | dis. | – | dis. | | dis. | + |
| CAU | | | | | prox. | + |
| | | | | | mid. | + |
| | | | | | dis. | |

FIG. 7

METHOD AND ELECTRONIC DEVICE FOR CLASSIFYING VESSEL

CROSS-REFERENCE TO RELATED APPLICATION

This application claims priority to Korean Patent Application No. 10-2023-0179487, filed in the Korean Intellectual Property Office on Dec. 12, 2023, the entire contents of which are hereby incorporated by reference.

BACKGROUND

Field

The present disclosure relates to a method and an electronic device for classifying vessels.

Description of Related Art

The coronary artery (or cardiovascular artery) surrounds the heart and can supply oxygen and nutrients to the heart muscle, known as the myocardium. Specifically, as oxygen and nutrients are continuously supplied to the myocardium from the coronary artery, the heart's function can be performed. Accordingly, if an abnormal condition (e.g., disease) occurs in the coronary artery, resulting in insufficient oxygen and nutrient supply to the myocardium, cardiovascular diseases such as myocardial infarction may develop.

The coronary artery is positioned in a way that it encircles the heart in a coronary shape and can be classified into detailed types based on its placement. For instance, the coronary artery can be categorized into the Right Coronary Artery (RCA), which begins from the initial section on the right side of the ascending aorta and primarily runs along the right side of the heart, and the Left Coronary Artery (LCA), which starts from the initial section of the left side of the ascending aorta and primarily runs along the left side of the heart. Furthermore, the Left Coronary Artery can be further divided into the Left Main Coronary Artery (LMCA, hereinafter referred to as LM), which originates from the upper left side of the heart, and branches into the Left Anterior Descending coronary artery (LAD) and the Left Circumflex coronary artery (LCX).

As described above, based on the shape in which the coronary artery is located, the coronary artery can supply oxygen and nutrients to the adjacent myocardium. Therefore, if an abnormal condition occurs in a part of the coronary artery, determining the specific area of the coronary artery affected by the abnormality, as well as the region of the myocardium associated with the abnormal coronary artery, allows for a more precise diagnosis of cardiovascular diseases.

Meanwhile, Coronary Angiography (CAG) can be used to observe whether an abnormality has occurred in the coronary artery. CAG involves injecting a contrast agent into the blood vessels of a subject (e.g., a patient) and using an X-ray imaging device (e.g., a C-arm X-ray imaging device) to capture images of the coronary artery. Through CAG images, the condition of the coronary artery can be observed, and cardiovascular diseases can be diagnosed.

Traditionally, assessing the condition of the coronary artery through CAG images relied on the experience of physicians or analysts. However, recently, techniques have been developed wherein an electronic device can diagnose cardiovascular diseases by receiving CAG images and analyzing them through machine learning. Nevertheless, due to the diversity of vascular types and structures, there is a need to develop technology capable of accurately classifying vessels to achieve more precise analysis.

SUMMARY

The present disclosure provides a method and an electronic device for classifying vessels to address the above-mentioned issues.

The present disclosure may be implemented in various forms, including a method, a device (system), and/or a computer program stored on a computer-readable storage medium.

According to an aspect of the present disclosure, a method of classifying vessels performed by at least one processor may include obtaining an image containing the cardiovascular vessels of a subject, and angle information of an image acquisition device relative to the subject; and identifying the type of at least one cardiovascular vessel contained in the image based on the angle information.

In an example, the angle information may include first rotation angle information of the image acquisition device around a first axis in the vertical direction of the subject, and second rotation angle information of the image acquisition device around a second axis in the horizontal direction of the subject.

According to an aspect, the step of identifying the type of at least one cardiovascular vessel may include identifying the type of at least one cardiovascular vessel in the image based on angle information and information related to types of cardiovascular vessels matched to the angle information.

In an example of the present disclosure, a method of classifying vessels performed by at least one processor may include obtaining an image containing the cardiovascular vessels of a subject and identifying the type of at least one cardiovascular vessel contained in the image through a machine learning model that takes the image as an input.

In an example, the machine learning model may be trained to limit the types of cardiovascular vessels identifiable in the image based on the angle information of the image acquisition device relative to the subject.

According to an aspect, the step of identifying the type of at least one cardiovascular vessel may further include correcting the identified type of at least one cardiovascular vessel based on the angle information of the image acquisition device relative to the subject.

According to an aspect, the vessel classification method may further include training a machine learning model to identify the view corresponding to each of a plurality of images capturing cardiovascular vessels by using as input the plurality of images, based on view information classified according to the angle information of the image acquisition device and class information where types of vessels matched to the view information are designated as a single class. The step of identifying the type of at least one cardiovascular vessel may include identifying the view corresponding to the image based on the machine learning model, and, based on the identified view, identifying the type of at least one cardiovascular vessel included in the image.

In an example, the class information may include at least one of a dummy class that contains only the type of vessel without any class or view information, enabling vessel classification even for images other than CAG images among the plurality of images.

According to an aspect, the step of identifying the type of at least one cardiovascular vessel may further include limiting the types of cardiovascular vessels that can be identified in the image based on the identified view.

In an example, the step of identifying the view corresponding to the image may include generating weights based on a predetermined number of points in the image, extracting at least one representative frame from the image based on the generated weights, inputting the at least one representative frame into a machine learning model, and identifying the view corresponding to the image based on the inference result for the at least one representative frame through the machine learning model.

According to an aspect, the step of identifying a view corresponding to an image based on the inference result of at least one representative frame may include, when the at least one representative frame comprises a plurality of representative frames, determining a final result through a voting method based on the inference results of the plurality of representative frames via the machine learning model, wherein the step of determining the final result includes, when a valid view is selected as a result of the voting based on the inference results of the plurality of representative frames, determining as the final result a class that includes the type of vessel and view information corresponding to the selected valid view; when an invalid view is selected as a result of the voting, re-voting is conducted on the remaining results excluding the invalid view from the inference results of the plurality of representative frames, and if a valid view is selected as a result of the re-voting, determining as the final result a class that includes the type of vessel and view information corresponding to the selected valid view; when an invalid view is selected as a result of the re-voting, conducting another re-voting on the remaining results excluding the invalid view from the inference results of the plurality of representative frames, and if all results of the re-voting are invalid views, conducting another voting with a second confidence level, and if a valid view is selected as a result of the subsequent voting, and determining as the final result a class that includes the type of vessel and view information corresponding to the selected valid view; and when an invalid view is selected as a result of the voting, conducting re-voting on the remaining results excluding the invalid view from the inference results of the plurality of representative frames, and if all results of the re-voting are invalid views, conducting another voting with a second confidence level, and if the result of this voting is an invalid view or an image that is not a CAG image, conducting a final re-voting with the first confidence level only on the view information of the class that includes the type of vessel from the initial inference results to determine the final result.

According to an aspect of the present disclosure, the electronic device may include a memory and at least one processor connected to the memory, configured to execute at least one computer-readable program contained in the memory, wherein the at least one program may include instructions to obtain an image containing the cardiovascular vessels of a subject and angle information of an image acquisition device relative to the subject, and to identify the type of at least one cardiovascular vessel included in the image based on the angle information.

In an example, the electronic device may include a main body with an embedded elevating driver, an elevating part fixed to the top of the elevating driver that elevates in a first direction, a rotating part that is rotatably connected at one end to the elevating part around a first axis in a second direction perpendicular to the first direction and has a curved surface formed at the other end, a C-shaped frame part slidably connected to the curved surface and provided in a C shape, an X-ray generating device positioned at one end of the C-shaped frame part, and an image acquisition device positioned at the other end of the C-shaped frame part.

In an example, the angle information may include first rotation angle information of the image acquisition device formed when the rotating part rotates around the first axis, and second rotation angle information of the image acquisition device formed when the C-shaped frame part slides, centered around a second axis in a third direction that is perpendicular to both the first and second directions.

According to an aspect of the present disclosure, in a non-transitory computer-readable recording medium stored with computer-readable instructions, the instructions, when executed by at least one processor, may cause the at least one processor to obtain an image containing the cardiovascular vessels of a subject and angle information of an image acquisition device relative to the subject, and to identify the type of at least one cardiovascular vessel included in the image based on the angle information.

According to some aspects of the present disclosure, by identifying the type of at least one cardiovascular vessel included in an image capturing the cardiovascular vessels of a subject based on the angle information of the image acquisition device relative to the subject, the accuracy of vessel classification may be enhanced, thereby enabling a more precise analysis of the image.

The effects of the present disclosure are not limited to those mentioned above, and other effects not explicitly stated may be clearly understood by those of ordinary skill in the art to which this disclosure pertains (referred to as "one of ordinary skill in the art") based on the descriptions in the claims.

BRIEF DESCRIPTION OF THE DRAWINGS

Embodiments of the present disclosure will be described with reference to the accompanying drawings explained below, where similar reference numbers indicate similar elements; however, the embodiments are not limited thereto.

FIG. 6 is a diagram showing information on types of the left coronary artery matched with angle information according to an example of the present disclosure.

FIG. 7 is a diagram showing information on types of the right coronary artery matched with angle information according to an example of the present disclosure.

DETAILED DESCRIPTION

Figure 1:
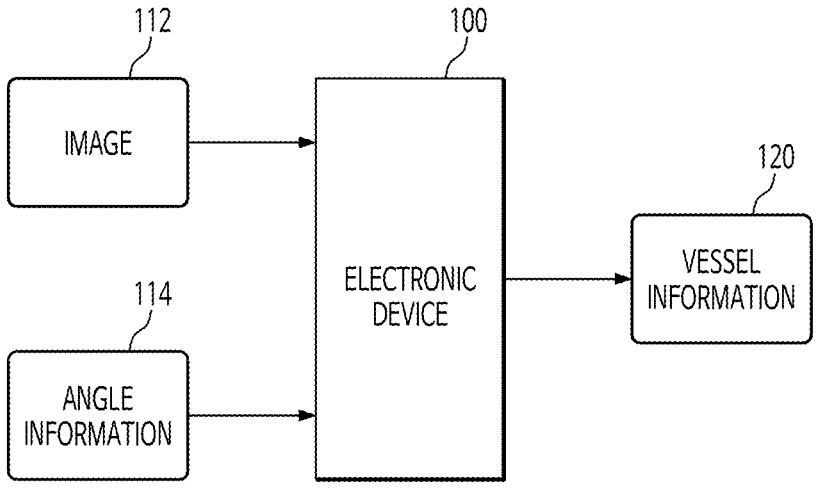
FIG. 1 is a diagram illustratively showing an electronic device for classifying vessels according to an example of the present disclosure.

Hereinafter, example details for the practice of the present disclosure will be described in detail with reference to the accompanying drawings. However, in the following description, detailed descriptions of well-known functions or configurations will be omitted if it may make the subject matter of the present disclosure rather unclear.

In the accompanying drawings, the same or corresponding components are assigned the same reference numerals. In addition, in the following description of various examples, duplicate descriptions of the same or corresponding components may be omitted. However, even if descriptions of components are omitted, it is not intended that such components are not included in any example.

Advantages and features of the disclosed examples and methods of accomplishing the same will be apparent by referring to examples described below in connection with the accompanying drawings. However, the present disclosure is not limited to the examples disclosed below, and may be implemented in various forms different from each other, and the examples are merely provided to make the present disclosure complete, and to fully disclose the scope of the disclosure to those skilled in the art to which the present disclosure pertains.

The terms used herein will be briefly described prior to describing the disclosed example(s) in detail. The terms used herein have been selected as general terms which are widely used at present in consideration of the functions of the present disclosure, and this may be altered according to the intent of an operator skilled in the art, related practice, or introduction of new technology. In addition, in specific cases, certain terms may be arbitrarily selected by the applicant, and the meaning of the terms will be described in detail in a corresponding description of the example(s). Accordingly, the terms used in this disclosure should be defined based on the meaning of the term and the overall content of the present disclosure, rather than simply the name of the term.

As used herein, the singular forms "a," "an," and "the" are intended to include the plural forms as well, unless the context clearly indicates the singular forms. Further, the plural forms are intended to include the singular forms as well, unless the context clearly indicates the plural forms. Further, throughout the description, when a portion is stated as "comprising (including)" a component, it is intended as meaning that the portion may additionally comprise (or include or have) another component, rather than excluding the same, unless specified to the contrary.

Further, the term "module" or "unit" used herein refers to a software or hardware component, and "module" or "unit" performs certain roles. However, the meaning of the "module" or "unit" is not limited to software or hardware. The "module" or "unit" may be configured to be in an addressable storage medium or configured to play one or more processors. Accordingly, as an example, the "module" or "unit" may include components such as software components, object-oriented software components, class components, and task components, and at least one of processes, functions, attributes, procedures, subroutines, program code segments, drivers, firmware, micro-codes, circuits, data, database, data structures, tables, arrays, and variables. Furthermore, functions provided in the components and the "modules" or "units" may be combined into a smaller number of components and "modules" or "units", or further divided into additional components and "modules" or "units."

A "module" or "unit" may be implemented as a processor and a memory, or may be implemented as a circuit (circuitry). Terms such as circuit and circuitry may refer to circuits in hardware, but may also refer to circuits in software. The "processor" should be interpreted broadly to encompass a general-purpose processor, a central processing unit (CPU), a microprocessor, a digital signal processor (DSP), a neural processing unit (NPU), a controller, a microcontroller, a state machine, etc. Under some circumstances, the "processor" may refer to an application-specific integrated circuit (ASIC), a programmable logic device (PLD), a field-programmable gate array (FPGA), etc. The "processor" may refer to a combination for processing devices, e.g., a combination of a DSP and a microprocessor, a combination of a plurality of microprocessors, a combination of one or more microprocessors in conjunction with a DSP core, or any other combination of such configurations. In addition, the "memory" should be interpreted broadly to encompass any electronic component that is capable of storing electronic information. The "memory" may refer to various types of processor-readable media such as random access memory (RAM), read-only memory (ROM), non-volatile random access memory (NVRAM), programmable read-only memory (PROM), erasable programmable read-only memory (EPROM), electrically erasable PROM (EE-PROM), flash memory, magnetic or optical data storage, registers, etc. The memory is said to be in electronic communication with a processor if the processor can read information from and/or write information to the memory. The memory integrated with the processor is in electronic communication with the processor.

In addition, terms such as first, second, A, B, (a), (b), etc. used in the following examples are only used to distinguish certain components from other components, and the nature, sequence, order, etc. of the components are not limited by the terms.

In addition, in the following examples, if a certain component is stated as being "connected," "combined" or "coupled" to another component, it is to be understood that there may be yet another intervening component "connected," "combined" or "coupled" between the two components, although the two components may also be directly connected or coupled to each other.

In addition, as used in the following examples, "comprise" and/or "comprising" does not foreclose the presence or addition of one or more other elements, steps, operations, and/or devices in addition to the recited elements, steps, operations, or devices.

Hereinafter, various examples of the present disclosure will be described in detail with reference to the accompanying drawings.

FIG. 1 is a diagram illustratively showing an electronic device 100 for classifying vessels according to an example of the present disclosure. Referring to FIG. 1, the electronic device 100 for classifying vessels may provide vessel information 120 based on the image 112 and angle information 114. For instance, the electronic device 100 may obtain the image 112 and angle information 114, identify the type of at least one vessel included in the image 112 based on the angle information 114, and provide vessel information 120 related to the identified at least one vessel. Here, the angle information 114 may represent the angle information of an image acquisition device relative to a subject (e.g., a patient) that captured the image 112.

The image 112 may include an image (e.g., a CAG image) that captures the cardiovascular vessels (or coronary arteries) of the subject. For example, the image 112 may include an image captured by an X-ray imaging device (e.g., a C-arm X-ray imaging device) of the cardiovascular vessels of the subject, taken after a contrast agent is injected into the subject's blood vessels. In this case, the angle information 114 may represent the angle information of the image acquisition device included in the X-ray imaging device relative to the subject, and the vessel information 120 may include information on at least one cardiovascular vessel identified in the image 112. The information on the cardiovascular vessels may, for example, include the type of the cardiovascular vessel. For ease of explanation, the following description assumes that the image 112 is a CAG image and that the angle information 114 is angle information of the image acquisition device included in the X-ray imaging device relative to the subject; however, the type of image 112 and the type of device for acquiring the image 112 are not limited thereto.

After the cardiovascular vessels of a subject are captured by an imaging device, the image 112 (e.g., cardiovascular angiography image) containing the cardiovascular vessels may be input to the electronic device 100. For example, the electronic device 100 may be connected to the imaging device via wired or wireless communication, and the image 112 may be provided from the imaging device to the electronic device 100 through a communication module. In some configurations, the electronic device 100 may be provided integrally with the imaging device. Alternatively, the electronic device 100 may receive the image 112 from an external electronic device (e.g., an external storage device) connected via a communication module. The method by which the electronic device 100 acquires the image 112 is not limited to the aforementioned examples and may be achieved in any manner.

The angle information 114 of the imaging device (or the imaging acquisition device included in the imaging device) relative to the subject may be input to the electronic device 100 along with the image 112 that captured the cardiovascular vessels of the subject, or after a certain time interval. For example, if the electronic device 100 is connected to the imaging device via wired or wireless communication, the imaging device may obtain the angle information 114 of the imaging device (or the imaging acquisition device included within the imaging device) relative to the subject at the time of capturing the image 112 and may provide the obtained angle information 114 along with the captured image 112 to the electronic device 100 through the communication module. In another example, if the electronic device 100 is integrally provided with the imaging device, the electronic device 100 may obtain the angle information 114 of the imaging device (or the imaging acquisition device included within the imaging device) relative to the subject along with the captured image 112 at the time the imaging device captures the image 112. In yet another example, the electronic device 100 may receive the angle information 114 along with the image 112 from an external electronic device (e.g., an external storage device) connected via a communication module.

the electronic device 100 may identify the type of at least one cardiovascular vessel in the image 112 containing the cardiovascular vessels of the subject, correct the identified type of at least one cardiovascular vessel based on the angle information 114, and then provide vessel information 120 for the at least one cardiovascular vessel. For example, after classifying vessels in the image 112, the electronic device 100 may verify errors in the vessel classification based on the angle information 114, and if an error in the vessel classification exists, it may correct the erroneous classification.

the electronic device 100 may limit (or set) the types of cardiovascular vessels that may be identified in the image 112 based on the angle information 114, identify the type of at least one cardiovascular vessel in the image 112 based on the limited types of cardiovascular vessels, and provide vessel information 120 related to the identified at least one cardiovascular vessel. For example, before classifying vessels in the image 112, the electronic device 100 may limit (or set) the types of cardiovascular vessels that may be identified in the image 112 based on the angle information 114. Then, the electronic device 100 may identify the type of at least one cardiovascular vessel included in the image 112 without deviating from the limited (or set) types of cardiovascular vessels.

Figure 2:
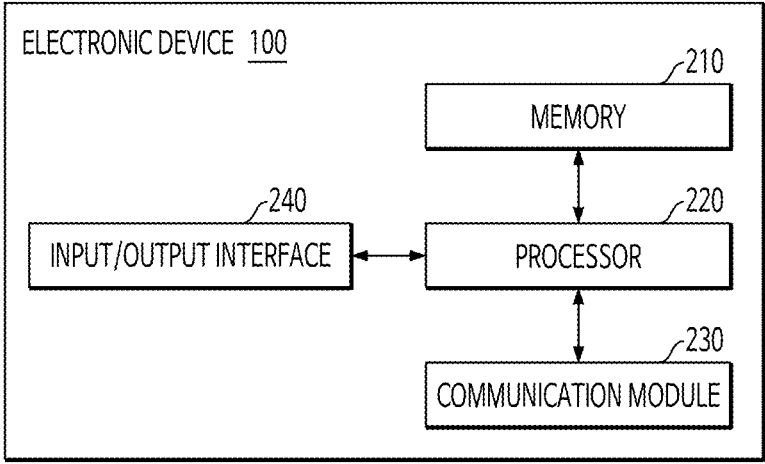
FIG. 2 is a diagram showing the internal configuration of the electronic device according to an example of the present disclosure.

FIG. 2 is a diagram showing the internal configuration of the electronic device 100 according to an example of the present disclosure. Referring to FIG. 2, the electronic device 100 may include a memory 210, a processor 220, a communication module 230, and an input/output interface 240. However, the configuration of the electronic device 100 is not limited thereto. According to various examples, the electronic device 100 may omit at least one of the aforementioned components and may further include at least one additional component. For example, the electronic device 100 may further include a display. In this case, the electronic device 100 may display at least one of images containing the cardiovascular vessels (e.g., image 112 in FIG. 1) or vessel information related to the cardiovascular vessels identified in the image (e.g., vessel information 120 in FIG. 1) on the display.

The memory 210 may store various data used by at least one other component of the electronic device 100 (e.g., the processor 220). The data may include, for example, input data or output data related to software (or programs) and associated commands.

The memory 210 may include any non-transitory computer-readable recording medium. The memory 210 may include permanent mass storage device, such as a disk drive, solid state drive (SSD), or flash memory. Alternatively, a permanent mass storage device, such as ROM, SSD, flash memory, or disk drive, may be included in the electronic device 100 as a separate permanent storage device distinct from the memory 210. Additionally, the memory 210 may store an operating system and at least one program code (e.g., instructions for image analysis and object identification processes installed and operated on the electronic device 100). Although the memory 210 is illustrated as a single memory in FIG. 2 for convenience of explanation, the memory 210 may include a plurality of memories and/or buffer memories.

Software components may be loaded from a computer-readable recording medium separate from the memory 210. Such a separate computer-readable recording medium may include a recording medium directly connectable to the electronic device 100, such as a computer-readable recording medium including a floppy drive, disk, tape, DVD/CD-ROM drive, or memory card. Alternatively, software components may be loaded into the memory 210 via the communication module 230 rather than a computer-readable recording medium. For example, at least one program may be loaded into the memory 210 based on a computer program (e.g., a program for transmitting data such as contrast images of cardiovascular vessels captured in angiography) that is installed by files provided by developers or a file distribution system that distributes installation files of applications through the communication module 230.

The processor 220 may execute software (or a program) to control at least one other component (e.g., hardware or software component) of the electronic device 100 connected to the processor 220 and may perform various data processing or computations. As at least a part of the data processing or computations, the processor 220 may load commands or data received from other components (e.g., the communication module 230) into volatile memory, process the commands or data stored in the volatile memory, and store the resulting data in non-volatile memory.

The processor 220 may be configured to process instructions of a computer program by performing basic arithmetic, logic, and input/output operations. The instructions may be provided by the memory 210 or the communication module 230 to the electronic device 100 or another external system. For example, the processor 220 may identify the type of at least one cardiovascular vessel included in a contrast image of the cardiovascular vessels. The processor 220 may then store the vessel information for the identified at least one cardiovascular vessel in the memory 210, output or display it on the display of the electronic device 100, or transmit it to an external electronic device through the communication module 230. Although the processor 220 is shown as a single processor in FIG. 2 for convenience of explanation, the processor 220 may include a plurality of processors.

The communication module 230 may support the establishment of a direct (e.g., wired) communication channel or a wireless communication channel between the electronic device 100 and an external electronic device, as well as performance of communication through the established communication channel. For example, the communication module 230 may provide configurations or functions that enable communication between the electronic device 100 and an external electronic device (e.g., a user terminal or cloud server) over a network. In one example, control signals, commands, and data provided under the control of the processor 220 of the electronic device 100 may be transmitted to an external electronic device via the communication module 130 and the network, and then through the communication module of the external electronic device. For instance, the electronic device 100 may receive an image capturing the cardiovascular vessels of a subject and angle information of the image acquisition device relative to the subject from an external electronic device through the communication module 230.

The input/output interface 240 may serve as a means for interfacing between the electronic device 100 and input or output devices (not shown) that may be connected to or included in the electronic device 100. For example, the input/output interface 240 may include a PCI express interface, an Ethernet interface, or the like; however, it is not limited thereto. Although FIG. 2 shows the input/output interface 240 as a component separate from the processor 220, it is not limited as such, and the input/output interface 240 may be configured to be included in the processor 220.

The processor 220 may perform functions related to vessel classification. To carry out functions related to vessel classification, the processor 220 may execute at least one computer-readable program included in the memory 210.

Here, the at least one program may include instructions to obtain an image capturing the cardiovascular vessels of a subject (e.g., image 112 in FIG. 1) and the angle information of the image acquisition device relative to the subject (e.g., angle information 114 in FIG. 1), and to identify the type of at least one cardiovascular vessel included in the image based on the angle information. The angle information of the image acquisition device relative to the subject may include first rotation angle information of the image acquisition device around a first axis in the vertical direction (or longitudinal direction) of the subject (e.g., direction connecting the head and feet) and second rotation angle information of the image acquisition device around a second axis in the lateral direction (or width direction) of the subject (e.g., direction connecting both shoulders or arms). Details on the angle information are described with reference to FIGS. 3 and 4. Additionally, for convenience in the following descriptions, the processor 220 executing at least one program to perform functions related to vessel classification may be described as the processor 220 performing vessel classification functions. For example, describing the at least one program as including instructions related to vessel classification functions may correspond to the description of the processor 220 performing vessel classification functions.

The processor 220 may identify the type of at least one cardiovascular vessel included in the image based on the angle information and the information related to the types of cardiovascular vessels matched to the angle information. The information related to the types of cardiovascular vessels matched to the angle information may, for instance, be information that defines (or sets) the types of cardiovascular vessels that may be identified in the captured image according to the image acquisition device's angle. In an example, the angle information and the information on types of cardiovascular vessels matched to the angle information may be pre-stored in the memory 210 as a table data structure. Detailed explanations of the angle information and the information on types of cardiovascular vessels matched to the angle information are provided with reference to FIGS. 6 and 7.

The processor 220 may identify the type of at least one cardiovascular vessel included in the image through a machine learning model that takes the image as input. Here, the machine learning model may be included in any accessible memory (e.g., memory 210 or the like) accessible by the processor 220. Additionally, the machine learning model may encompass any model used for inferring an answer to a given input. In an example, the machine learning model may include an artificial neural network model comprising an input layer, a plurality of hidden layers, and an output layer. Each layer may contain one or more nodes. Furthermore, the machine learning model may include weights associated with the plurality of nodes contained in the model, where the weights may include any parameters associated with the machine learning model. The machine learning model of the present disclosure may be a model trained using various learning methods. For example, various learning methods such as supervised learning, semi-supervised learning, unsupervised learning (or self-learning), and reinforcement learning may be utilized in the present disclosure. In the present disclosure, the machine learning model may refer to an artificial neural network model, and the artificial neural network model may refer to the machine learning model. Detailed explanations of the artificial neural network model are provided with reference to FIG. 11.

Figure 3:
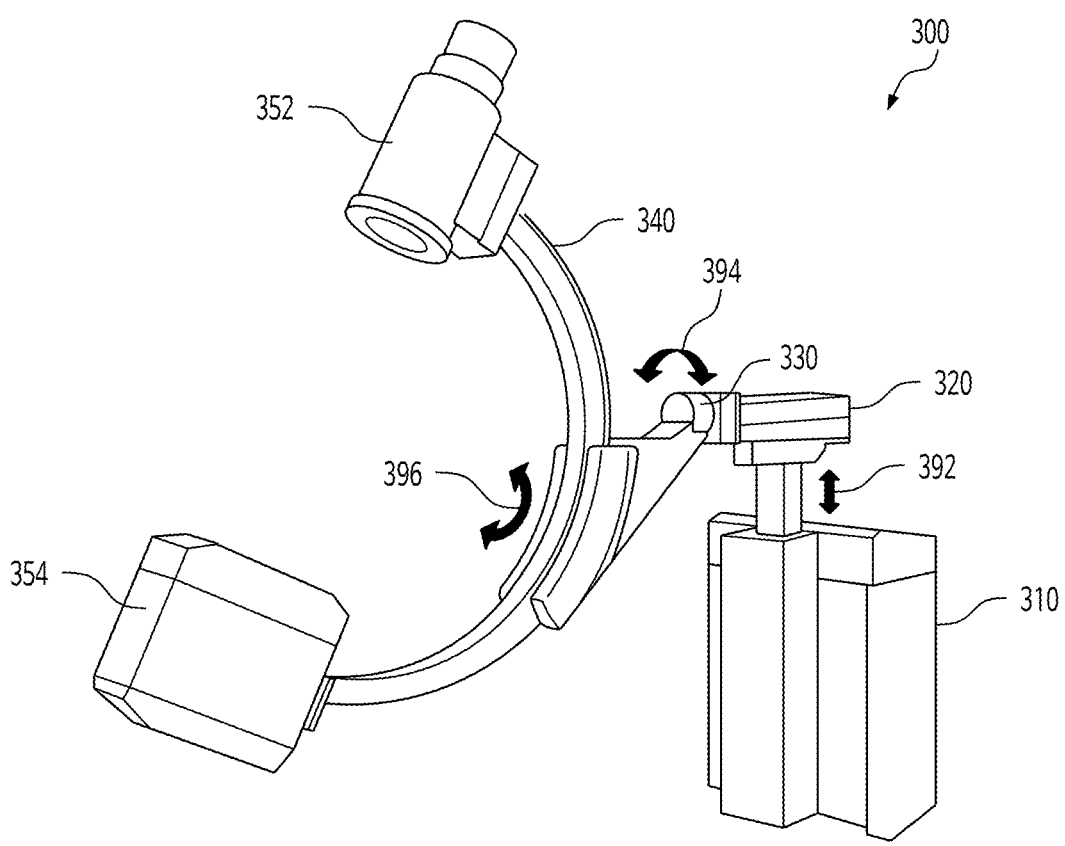
FIG. 3 is a perspective view of an electronic device including an image acquisition device according to an example of the present disclosure.

FIG. 3 is a perspective view of an electronic device 300 including an image acquisition device according to an example of the present disclosure. The electronic device 300 shown in FIG. 3 includes an image acquisition device 352 for acquiring an image (e.g., image 112 in FIG. 1) by capturing the cardiovascular vessels of a subject and may be connected to the electronic device 100 in FIG. 1 through a communication module or may be provided integrally with the electronic device 100 in FIG. 1. For example, the electronic device 300 may be an X-ray imaging device.

Referring to FIG. 3, the electronic device 300 may include a main body 310, an elevating part 320, a rotating part 330, a C-shaped frame part 340, an X-ray generating device 354, and an image acquisition device 352. However, the configuration of the electronic device 300 is not limited thereto. The electronic device 300 may be provided in any configuration or form as long as it includes the image acquisition device 352.

The main body 310 may include an embedded elevating driver. The main body 310 may also include a controller (e.g., a processor) for controlling the configuration of the electronic device 300. Additionally, if the electronic device 300 is connected to the electronic device 100 in FIG. 1 via a communication module, the main body 310 may include the communication module.

The elevating part 320 is fixed to the top of the elevating driver embedded in the main body 310 and may be elevated in a first direction 392 (e.g., vertical direction). For example, the elevating part 320 may be adjusted to match the height of the examination target (or imaging target) (e.g., the heart) based on the posture of the subject.

The rotating part 330 may be connected to the elevating part 320 such that one end of the rotating part 330 may be rotatably connected 394 about a first axis in a second direction perpendicular to a first direction 392, and the other end may include a curved surface. When the rotating part 330 rotates 394 about the first axis, the rotation angle (e.g., the first rotation angle) of the image acquisition device 352 may change. Here, the first axis may be the axis in the up-down direction (or longitudinal direction) of the subject (e.g., the direction connecting the head and the feet of the subject) or an axis parallel to it. For instance, the rotation 394 of the rotating part 330 about the first axis may indicate that the image acquisition device 352 rotates about the first axis, and the rotation of the image acquisition device 352 about the first axis may signify that the image acquisition device 352 rotates around the torso (or heart) of the subject in the left-right direction. In the following description, the rotation angle information of the image acquisition device 352 formed when the rotating part 330 rotates 394 about the first axis may be referred to as the first rotation angle information.

The C-shaped frame part 340 is slidably connected 396 to the curved surface formed on the rotating part 330 and may be configured in a C shape (or a ring shape with a partial cutout). Due to the shape of the C-shaped frame part 340, the electronic device 300 may be referred to as a C-arm or C-arm imaging device. When the C-shaped frame part 340 slides 396 along the curved surface of the rotating part 330, the rotation angle of the image acquisition device 352 (e.g., the second rotation angle) may change. When the C-shaped frame part 340 slides 396 along the curved surface of the rotating part 330, the image acquisition device 352 may rotate around a second axis in a third direction perpendicular to both the first direction 392 and the second direction. Here, the second axis may be the axis in the lateral direction (or width direction) of the subject (e.g., the direction connecting both shoulders or arms) or an axis parallel to it. For example, the sliding 396 of the C-shaped frame part 340 along the curved surface of the rotating part 330 may indicate that the image acquisition device 352 rotates around the second axis, and the rotation of the image acquisition device 352 around the second axis may represent the image acquisition device 352 rotating vertically around the torso (or heart) of the subject. In the following description, the rotation angle information of the image acquisition device 352 formed when the C-shaped frame part 340 slides 396 along the curved surface of the rotating part 330 may be referred to as the second rotation angle information.

The X-ray generating device 354 may be positioned at one end of the C-shaped frame part 340, while the image acquisition device 352 may be positioned at the other end of the C-shaped frame part 340. The X-ray generating device 354 may generate X-rays and transmit them through the examination target (or imaging target), and the image acquisition device 352 may detect the amount of transmitted X-rays and perform signal processing to acquire an image (e.g., image 112 in FIG. 1). At this time, the electronic device 300 may acquire the angle information of the image acquisition device 352 (e.g., first rotation angle information and second rotation angle information) (e.g., angle information 114 in FIG. 1) at the time of capturing the image, along with the image acquired through the image acquisition device 352.

Figure 4:
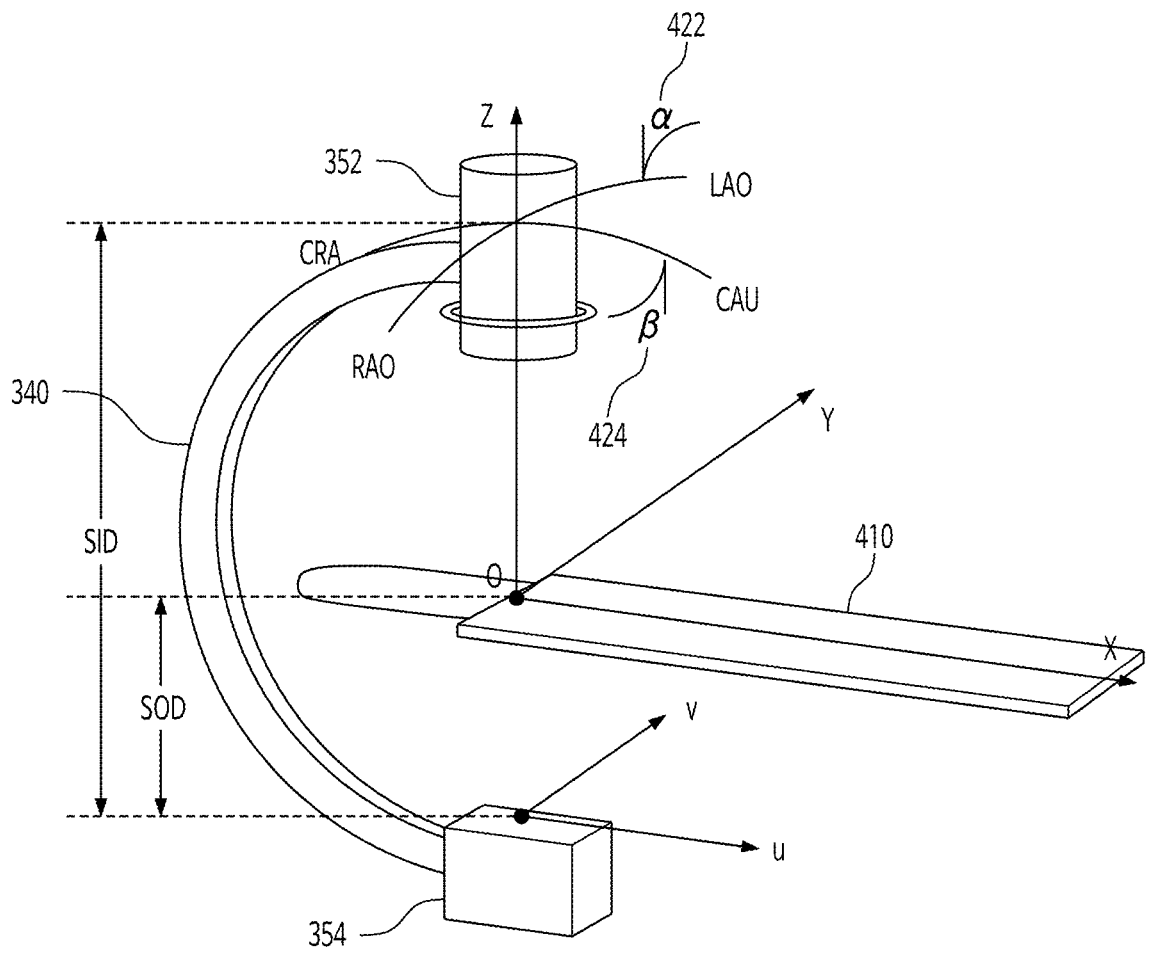
FIG. 4 is a diagram illustrating the angle information of an image acquisition device relative to a subject according to an example of the present disclosure.

FIG. 4 is a diagram illustrating the angle information of the image acquisition device 352 relative to the subject according to an example of the present disclosure. Referring to FIG. 4, the X-ray imaging device (or C-arm or C-arm imaging device) (e.g., electronic device 300 in FIG. 3) may adjust (or set) the angles 422 and 424 of the image acquisition device 352 to correspond to the cardiovascular region to be imaged, in order to identify the area where an abnormality has occurred concerning the cardiovascular vessels of the subject. As described with reference to FIG. 3, the X-ray imaging device may have the X-ray generating device 354 and the image acquisition device 352 positioned at each end of the C-shaped frame part 340. By sliding the C-shaped frame part 340 along the curved surface of the rotating part (e.g., rotating part 330 in FIG. 3) (e.g., sliding 396 in FIG. 3) or by rotating the rotating part (e.g., rotating 394 in FIG. 3), the angles 422 and 424 of the image acquisition device 352 may be adjusted.

The angles 422 and 424 of the image acquisition device 352 may be set based on the examination target (or imaging target). For example, when the subject is lying on the examination table 410, the vertical (or longitudinal) direction of the subject (e.g., the direction connecting the head and feet) may correspond to the X-axis direction, and the lateral (or width) direction of the subject (e.g., the direction connecting both shoulders or both arms) may correspond to the Y-axis direction. Specifically, the direction from the head to the feet may be the (+)X-axis direction, while the direction from the feet to the head may be the (−)X-axis direction. Likewise, the direction from the right shoulder (or right arm) to the left shoulder (or left arm) may be the (+)Y-axis direction, and the direction from the left shoulder (or left arm) to the right shoulder (or right arm) may be the (−)Y-axis direction. In this case, the first rotation angle information of the image acquisition device 352, formed when the rotating part rotates to rotate the image acquisition device 352 around the X-axis, may be set as the first rotation angle α 422, and the second rotation angle information of the image acquisition device 352, formed when the C-shaped frame part 340 slides along the curved surface of the rotating part to rotate the image acquisition device 352 around the Y-axis, may be set as the second rotation angle β 424.

The first rotation angle 422 may be referred to as the primary angle. When the first rotation angle 422 has a rotation angle in the (−)Y-axis direction, the image may be described as having a right anterior oblique (RAO) view, and the first rotation angle 422 may be expressed as an RAO angle. Additionally, when the first rotation angle 422 has a rotation angle in the (+)Y-axis direction, the image may be described as having a left anterior oblique (LAO) view, and the first rotation angle 422 may be expressed as an LAO angle. When the first rotation angle 422 has a rotation angle centered on the Y-axis (i.e., 0 degrees), the image may be described as having an anterior-posterior (AP) view.

The second rotation angle 424 may be referred to as the secondary angle. When the second rotation angle 424 has a rotation angle in the (−)X-axis direction, the image may be described as having a CRA (or CRANIAL) view, and the second rotation angle 424 may be expressed as a CRA angle. Additionally, when the second rotation angle 424 has a rotation angle in the (+)X-axis direction, the image may be described as having a CAU (or CAUDAL) view, and the second rotation angle 424 may be expressed as a CAU angle.

According to an aspect, the type of cardiovascular vessel to be observed in the image or included in the image may be set through a combination of the first rotation angle 422 and the second rotation angle 424. Detailed explanations of the types of cardiovascular vessels that may be set through combinations of the first rotation angle 422 and the second rotation angle 424 are provided with reference to FIGS. 6 and 7.

Figure 5:
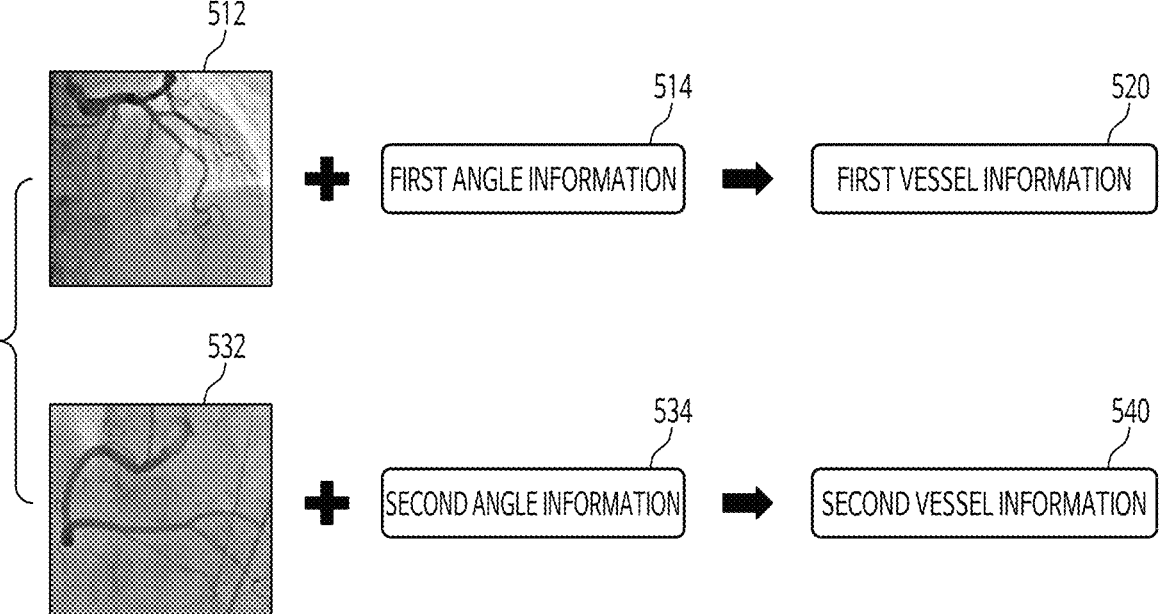
FIG. 5 is a diagram for explaining a method of classifying vessels based on an image and angle information according to an example of the present disclosure.

FIG. 5 is a diagram for explaining a method of classifying vessels based on an image and angle information according to an example of the present disclosure. The X-ray imaging device (or C-arm or C-arm imaging device) (e.g., electronic device 300 in FIG. 3) may adjust (or set) the angle (e.g., angles 422 and 424 in FIG. 4) of the image acquisition device (e.g., image acquisition device 352 in FIGS. 3 and 4) to correspond to the cardiovascular region to be imaged to identify the area where an abnormality has occurred concerning the cardiovascular vessels of the subject. Additionally, when the image acquisition device captures the cardiovascular vessels of the subject, the X-ray imaging device may transmit the captured image (e.g., CAG image) and the angle information of the image acquisition device at the time of capture to the electronic device (e.g., electronic device 100 in FIGS. 1 and 2). Here, since the X-ray imaging device (e.g., electronic device 300 in FIG. 3) and the electronic device that provides vessel information in the image (e.g., electronic device 100 in FIGS. 1 and 2) may be provided integrally or may operate in conjunction, for convenience, the following description will describe them collectively as the electronic device.

Referring to FIG. 5, the electronic device may identify the type of at least one cardiovascular vessel included in the images 512 and 532 based on the acquired image 512 and 532, and the angle information 514 and 534 of the image acquisition device relative to the subject at the time of capturing images 512 and 532, and provide vessel information 520 and 540 related to the identified at least one cardiovascular vessel. For example, the electronic device may identify the type of at least one cardiovascular vessel included in the first image 512 based on the first image 512, and the first angle information 514 of the image acquisition device relative to the subject at the time of capturing the first image 512, and provide the first vessel information 520 related to the identified at least one cardiovascular vessel. Additionally, the electronic device may identify the type of at least one cardiovascular vessel included in the second image 532 based on the second image 532, and the second angle information 534 of the image acquisition device relative to the subject at the time of capturing the second image 532, and provide the second vessel information 540 related to the identified at least one cardiovascular vessel. However, the number of images and the corresponding angle information of the image acquisition device relative to the subject at the time of capturing each image that may be used for vessel classification is not limited thereto. For instance, although not illustrated, the electronic device may identify at least one type of cardiovascular vessel included in at least one other image, based on the at least one other image, distinct from the first image 512 and the second image 532, and the angle information of the image acquisition device relative to the subject at the time of capturing the at least one other image, and provide vessel information for the identified at least one cardiovascular vessel.

After identifying the type of at least one cardiovascular vessel in images 512 and 532, the electronic device may correct the identified at least one cardiovascular vessel type based on the angle information 514 and 534. The electronic device may then provide vessel information 520 and 540 for the at least one cardiovascular vessel. For example, after classifying vessels in images 512 and 532, the electronic device may verify the vessel classification errors based on the angle information 514 and 534, and if any errors in vessel classification are detected, it may correct these errors.

The electronic device may restrict (or set) the types of cardiovascular vessels that may be identified in images 512 and 532 based on angle information 514 and 534, and then identify the type of at least one cardiovascular vessel in images 512 and 532 based on the restricted types of cardiovascular vessels. The electronic device may then provide vessel information 520 and 540 for the identified at least one cardiovascular vessel. For example, before classifying vessels in images 512 and 532, the electronic device may restrict (or set) the types of cardiovascular vessels that may be identified in images 512 and 532 based on angle information 514 and 534, and identify the type of at least one cardiovascular vessel in images 512 and 532 so as not to deviate from the restricted (or set) types of cardiovascular vessels.

FIG. 6 is a diagram showing information on types of left coronary arteries matched to angle information according to an example of the present disclosure. The X-ray imaging device (or C-arm or C-arm imaging device) (e.g., electronic device 300 in FIG. 3) may set different types of cardiovascular vessels to be included in the image (e.g., CAG image) according to the angle (e.g., angles 422 and 424 in FIG. 4) of the image acquisition device (e.g., image acquisition device 352 in FIGS. 3 and 4). FIG. 6 illustrates types of left coronary arteries that may be set based on various combinations of the first rotation angle α and second rotation angle β of the image acquisition device. Although FIG. 6 shows the angle information of the image acquisition device and information on the types of left coronary arteries matched to the angle information in a table data structure, the data structure is not limited thereto.

Referring to FIG. 6, when the first rotation angle α has an RAO angle and the second rotation angle β has a CRA angle, that is, when the first rotation angle of the image acquisition device has a rotation angle in the (−)Y-axis direction and the second rotation angle has a rotation angle in the (−)X-axis direction, the image may have an RAO CRANIAL view. In an RAO CRANIAL view, the left anterior descending artery (LAD) may be identified in the image. In the table of FIG. 6, a "+" symbol in identification levels may indicate that identification is possible, "++" may indicate clear identification, and "−" may indicate difficulty in identification. For instance, if the levels of identification denoted by "+", "++", and "−" are set as the first, second, and third identification levels respectively, the second identification level would have the highest value, the third identification level would have the lowest value, and the first identification level would have a value between the second and third. Additionally, in the table of FIG. 6, "LAD-p" may refer to the proximal portion of the left anterior descending artery, "LAD-m" may indicate the middle portion, and "LAD-d" may denote the distal portion. Similarly, in the table of FIG. 6, "LCX-p" may represent the proximal portion of the left circumflex artery, and "LCX-d" may indicate the distal portion. For example, when the image has an RAO CRANIAL view, the middle and distal portions of the left anterior descending artery may be most clearly identifiable, the proximal portion of the left anterior descending artery may be identifiable, and the proximal and distal portions of the left circumflex artery may be difficult to identify.

When the first rotation angle α has an AP angle and the second rotation angle β has a CRA angle, that is, when the first rotation angle of the image acquisition device is 0 degrees and the second rotation angle of the image acquisition device has a rotation angle in the (−)X-axis direction, the image may have an AP CRANIAL view. In an AP CRANIAL view, the proximal, middle, and distal portions of the left anterior descending artery may be identifiable in the image, while the proximal and distal portions of the left circumflex artery may be difficult to identify.

When the first rotation angle α has an LAO angle and the second rotation angle β has a CRA angle, that is, when the first rotation angle of the image acquisition device has a rotation angle in the (+)Y-axis direction and the second rotation angle of the image acquisition device has a rotation angle in the (−)X-axis direction, the image may have an LAO CRANIAL view. In an LAO CRANIAL view, the left main coronary artery (LM), as well as the proximal, middle, and distal portions of the left anterior descending artery, may be identifiable in the image, while the proximal and distal portions of the left circumflex artery may be difficult to identify.

When the first rotation angle α has an AP angle and the second rotation angle β is 0 degrees, that is, when both the first and second rotation angles of the image acquisition device are 0 degrees, the image may have an AP view. In an AP view, the left anterior descending artery may be identifiable in the image.

When the first rotation angle α has an RAO angle and the second rotation angle β has a CAU angle, that is, when first rotation angle of the image acquisition device has a rotation angle in the (−)Y-axis direction and the second rotation angle of the image acquisition device has a rotation angle in the (+)X-axis direction, the image may have an RAO CAUDAL view. In an RAO CAUDAL view, the left main coronary artery, the proximal portion of the left anterior descending artery, and both the proximal and distal portions of the left circumflex artery may be identifiable, while the middle and distal portions of the left anterior descending artery may be difficult to identify.

When the first rotation angle α has an AP angle and the second rotation angle β has a CAU angle, that is, when the first rotation angle of the image acquisition device is 0 degrees and the second rotation angle of the image acquisition device has a rotation angle in the (+)X-axis direction, the image may have an AP CAUDAL view. In an AP CAUDAL view, the left main coronary artery may be most clearly identifiable, while the proximal portion of the left anterior descending artery, as well as both the proximal and distal portions of the left circumflex artery, may be identifiable. However, the middle and distal portions of the left anterior descending artery may be difficult to identify.

When the first rotation angle α has an LAO angle and the second rotation angle β has a CAU angle, that is, the first rotation angle of the image acquisition device has a rotation angle in the (+)Y-axis direction and the second rotation angle of the image acquisition device has a rotation angle in the (+)X-axis direction, the image may have an LAO CAUDAL view. The LAO CAUDAL view may be referred to as the SPIDER view. In an LAO CAUDAL view, the left main coronary artery may be most clearly identifiable in the image, while the proximal portion of the left anterior descending artery and the proximal portion of the left circumflex artery may be identifiable. However, the middle and distal portions of the left anterior descending artery and the distal portion of the left circumflex artery may be difficult to identify in the image.

The electronic device (e.g., electronic device 100 in FIGS. 1 and 2) may, in the process of identifying types of cardiovascular vessels in an image, process the image so that types of cardiovascular vessels that are designated as difficult to identify (e.g., marked with a "−" symbol) in the aforementioned table are not identified. For example, the electronic device may process (or restrict) images with an RAO CRANIAL view so that the left circumflex artery is not identified.

FIG. 7 is a diagram showing information on types of the right coronary artery matched with angle information according to an example of the present disclosure. Referring to FIG. 7, the X-ray imaging device (or C-arm or C-arm imaging device) (e.g., electronic device 300 in FIG. 3) may adjust the types of cardiovascular vessels included in the image (e.g., CAG image) based on the angle (e.g., angles 422 and 424 in FIG. 4) of the image acquisition device (e.g., image acquisition device 352 in FIGS. 3 and 4). FIG. 7 illustrates the types of right coronary arteries that may be set through combinations of the first rotation angle α and second rotation angle β of the image acquisition device. Although FIG. 7 shows the angle information of the image acquisition device and the information on types of right coronary arteries matched to the angle information in a table data structure, but the data structure is not limited thereto.

Referring to FIG. 7, when the first rotation angle α has an RAO angle and the second rotation angle β has a CRA angle, that is, the first rotation angle of the image acquisition device has a rotation angle in the (−)Y-axis direction and the second rotation angle of the image acquisition device has a rotation angle in the (−)X-axis direction, the image may have an RAO CRANIAL view. In the table in FIG. 7, a "+" symbol may indicate that identification is possible, "++" may indicate clear identification, and "−" may indicate difficulty in identification. Additionally, in the table in FIG. 7, "prox." represents the proximal portion, "mid." represents the middle portion, and "dis." represents the distal portion. For example, when the image has an RAO CRANIAL view, the proximal portion of the right coronary artery may be most clearly identifiable in the image, while the middle portion of the right coronary artery may be identifiable.

When the first rotation angle α has an AP angle and the second rotation angle β has a CRA angle, that is, the first rotation angle of the image acquisition device is 0 degrees and the second rotation angle has a rotation angle in the (−)X-axis direction, the image may have an AP CRANIAL view. In an AP CRANIAL view, the distal portion of the right coronary artery may be most clearly identifiable, while the middle portion of the right coronary artery may be identifiable.

When the first rotation angle α has an LAO angle and the second rotation angle β has a CRA angle, that is, the first rotation angle of the image acquisition device has a rotation angle in the (+)Y-axis direction and the second rotation angle of the image acquisition device has a rotation angle in the (−)X-axis direction, the image may have an LAO CRANIAL view. In an LAO CRANIAL view, the proximal portion of the right coronary artery may be most clearly identifiable in the image, while the middle and distal portions of the right coronary artery may be identifiable.

When the first rotation angle α has an RAO angle and the second rotation angle β is 0 degrees, that is, the first rotation angle of the image acquisition device has a rotation angle in the (−)Y-axis direction and the second rotation angle of the image acquisition device is 0 degrees, the image may have an RAO view. In an RAO view, the middle portion of the right coronary artery may be most clearly identifiable in the image, while the proximal and distal portions of the right coronary artery may be difficult to identify.

When the first rotation angle α has an LAO angle and the second rotation angle β is 0 degrees, that is, the first rotation angle of the image acquisition device has a rotation angle in the (+)Y-axis direction and the second rotation angle of the image acquisition device is 0 degrees, the image may have an LAO view. In an LAO view, the proximal, middle, and distal portions of the right coronary artery may be identifiable in the image.

When the first rotation angle α has an LAO angle and the second rotation angle β has a CAU angle, that is, the first rotation angle of the image acquisition device has a rotation angle in the (+)Y-axis direction and the second rotation angle of the image acquisition device has a rotation angle in the (+)X-axis direction, the image may have an LAO CAUDAL view. In an LAO CAUDAL view, the proximal and middle portions of the right coronary artery may be identifiable in the image.

The electronic device (e.g., electronic device 100 in FIGS. 1 and 2) may, during the process of identifying the types of cardiovascular vessels in an image, process the image so that cardiovascular vessel types designated as difficult to identify (e.g., marked with a "−" symbol) in the aforementioned table are not identified. For example, the electronic device may process (or restrict) images with an RAO view so that the proximal portion and distal portion of the right coronary artery are not identified.

Figure 8:
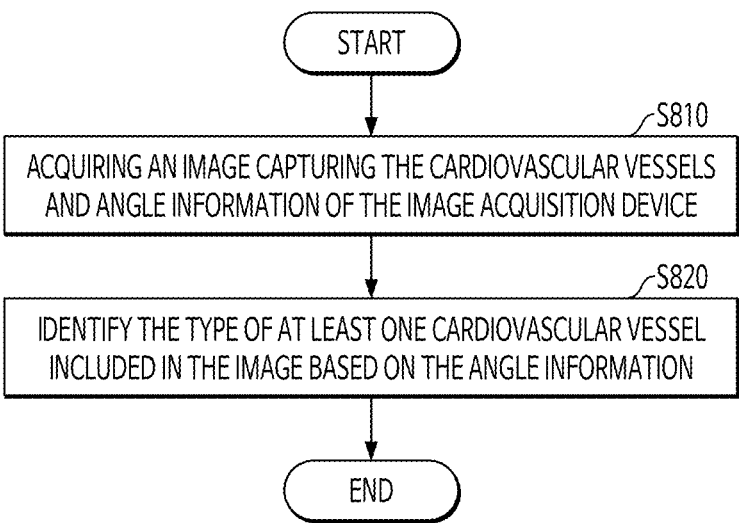
FIG. 8 is a diagram for explaining a method of classifying vessels according to an example of the present disclosure.

FIG. 8 is a diagram for explaining a method of classifying vessels according to an example of the present disclosure. Referring to FIG. 8, in step 810 (S810), the processor (e.g., processor 220 in FIG. 2) of the electronic device for vessel classification (e.g., electronic device 100 in FIGS. 1 and 2) may acquire an image capturing the cardiovascular vessels of a subject (e.g., image 112 in FIG. 1) and angle information of the image acquisition device (e.g., image acquisition device 352 in FIGS. 3 and 4) relative to the subject (e.g., angle information 114 in FIG. 1 or angles 422 and 424 in FIG. 4). Here, the angle information of the image acquisition device relative to the subject may include first rotation angle information of the image acquisition device around a first axis (e.g., X-axis in FIG. 4) in the vertical direction (or longitudinal direction) of the subject (e.g., the direction connecting the head and feet), and second rotation angle information of the image acquisition device around a second axis (e.g., Y-axis in FIG. 4) in the lateral direction (or width direction) of the subject (e.g., the direction connecting both shoulders or arms). The processor may acquire the image and angle information either simultaneously or at certain time intervals.

In step 820 (S820), the processor may identify the type of at least one cardiovascular vessel included in the image based on the angle information. The processor may identify the type of at least one cardiovascular vessel in the image based on the angle information and information on the types of cardiovascular vessels matched to the angle information. Here, the information on the types of cardiovascular vessels matched to the angle information may be the information that defines (or sets) the types of cardiovascular vessels that may be identified in the captured image based on the image acquisition device's capture angle. In an example, the angle information and the information on types of cardiovascular vessels matched with the angle information may be pre-stored in the memory of the electronic device (e.g., memory 210 in FIG. 2) as a table data structure.

After identifying the type of at least one cardiovascular vessel in the image, the processor may correct the identified at least one cardiovascular vessel type based on the angle information. For example, after classifying vessels in the image, the processor may verify errors of the vessel classification based on the angle information and correct any erroneous classifications if errors are detected.

The processor may restrict (or set) the types of cardiovascular vessels that may be identified in the image based on the angle information and then identify the type of at least one cardiovascular vessel in the image based on the restricted types of cardiovascular vessels. For instance, before classifying vessels in the image, the processor may restrict (or set) the types of cardiovascular vessels that may be identified in the image based on the angle information, and identify the type of the at least one cardiovascular vessel in the image so that the vessel type does not deviate from the restricted (or set) types.

Figure 9:
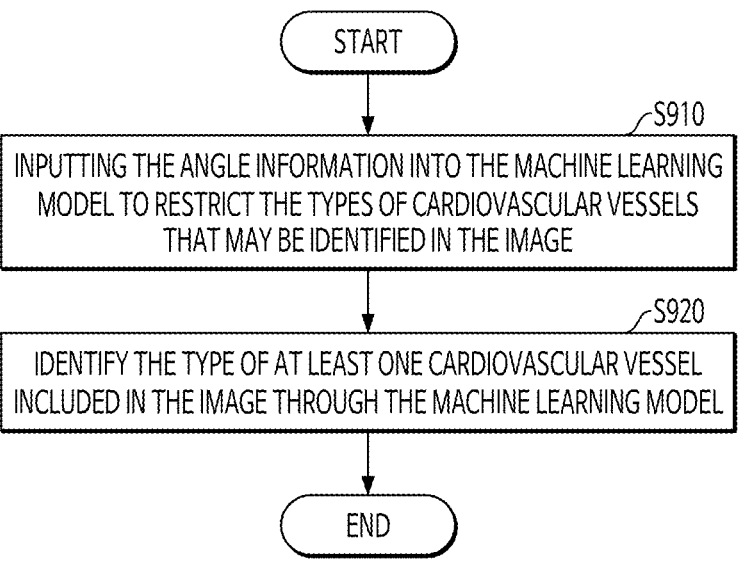
FIG. 9 is a diagram for explaining a method of limiting the types of cardiovascular vessels identifiable in an image based on angle information according to an example of the present disclosure.

FIG. 9 is a diagram for explaining a method of restricting the types of cardiovascular vessels that may be identified in an image based on angle information according to an example of the present disclosure. The processor (e.g., processor 220 in FIG. 2) of the electronic device for vessel classification (e.g., electronic device 100 in FIGS. 1 and 2) may identify the type of at least one cardiovascular vessel included in the image capturing the cardiovascular vessels of a subject (e.g., image 112 in FIG. 1) based on the captured image, and angle information of the image acquisition device relative to the subject (e.g., angle information 114 in FIG. 1 or angles 422 and 424 in FIG. 4). In this process, the processor may identify the type of at least one cardiovascular vessel in the image through a machine learning model (e.g., a vessel classification model) that takes the image as input.

Referring to FIG. 9, in step 910 (S910), the processor may input the angle information into the machine learning model to restrict the types of cardiovascular vessels that may be identified in the image. For example, when additional angle information is input into the machine learning model, it may be trained to restrict the types of cardiovascular vessels that may be identified in the image based on the angle information.

In step 920 (S920), the processor may identify the type of at least one cardiovascular vessel included in the image through the machine learning model. For example, the machine learning model may identify the type of at least one cardiovascular vessel in the image based on the restricted types of cardiovascular vessels. That is, the machine learning model may identify the type of at least one cardiovascular vessel in the image so that the identification does not deviate from the restricted (or set) types.

The machine learning model used in steps 910 and 920 may be the same machine learning model. For example, the machine learning model may include a machine learning model that takes both the image and angle information as inputs simultaneously, allowing it to restrict the types of vessels and classify vessels in the image.

The machine learning models used in steps 910 and 920 may be different machine learning models from each other. For example, the machine learning model used in step 910 may include a machine learning model that receives angle information as input and outputs information about the types of vessels whose identification is restricted in the image, while the machine learning model used in step 920 may include a machine learning model that receives the image and information about the types of vessels whose identification is restricted in the image as input and classifies the vessels in the image.

Figure 10:
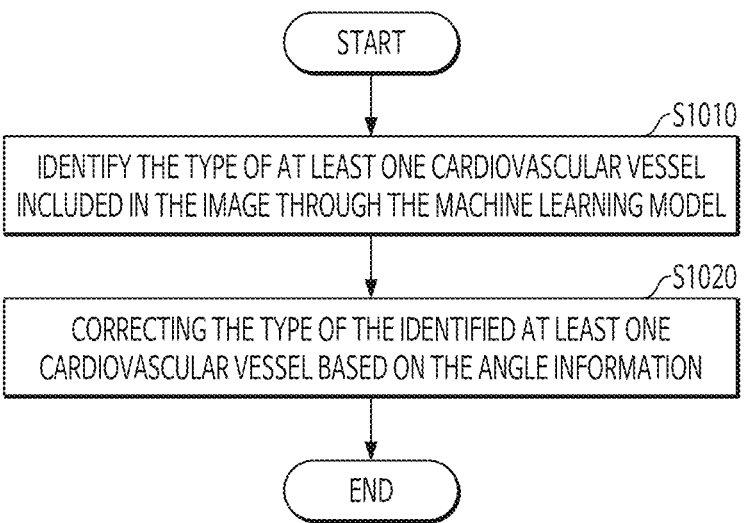
FIG. 10 is a diagram for explaining a method of correcting the identified type of cardiovascular vessels based on angle information according to an example of the present disclosure.

FIG. 10 is a diagram for explaining a method of correcting identified types of cardiovascular vessels based on angle information according to an example of the present disclosure. The processor (e.g., processor 220 in FIG. 2) of the electronic device for vessel classification (e.g., electronic device 100 in FIGS. 1 and 2) may identify the type of at least one cardiovascular vessel included in the image capturing the cardiovascular vessels of a subject (e.g., image 112 in FIG. 1) based on the captured image, and angle information of the image acquisition device (e.g., the image acquisition device 352 in FIGS. 3 and 4) relative to the subject (e.g., angle information 114 in FIG. 1 or angles 422 and 424 in FIG. 4). In this process, the processor may identify the type of at least one cardiovascular vessel in the image through a machine learning model (e.g., a vessel classification model) that takes the image as input.

Referring to FIG. 10, in step 1010 (S1010), the processor may identify the type of at least one cardiovascular vessel included in the image through the machine learning model. For example, the machine learning model may identify the type of at least one cardiovascular vessel in the input image.

In step 1020 (S1020), the processor may correct the type of the identified at least one cardiovascular vessel based on the angle information. For example, the processor may make corrections to the identified at least one cardiovascular vessel type based on the angle information. The processor may utilize a machine learning model to correct the identified cardiovascular vessel type based on the angle information. In this case, the machine learning model which may be used in step 1020 may be the same as the machine learning model used in step 1010. For instance, the machine learning model may simultaneously take both the image and angle information as inputs, classify vessels in the image, verify any errors in vessel classification, and correct errors if any are detected. Alternatively, the machine learning model used in step 1020 may differ from the machine learning model used in step 1010. For example, the machine learning model used in step 1010 may classify vessels in the image based on the input image, while the machine learning model used in step 1020 may receive vessel classification information (e.g., the image with classified vessels) and angle information as inputs to verify errors in vessel classification and correct those errors if they exist.

The processor may classify the view of the image based on angle information. Here, the angle information may include the first and second rotation angles of the image acquisition device, wherein the first rotation angle represents the rotation angle along the lateral direction (or width direction) of the subject (e.g., the direction connecting both shoulders or arms, hereinafter referred to as the Y-axis direction), while the second rotation angle represents the rotation angle along the vertical direction (or longitudinal direction) of the subject (e.g., the direction connecting the head and feet, hereinafter referred to as the X-axis direction). For example, for the right coronary artery, the processor may classify the view as follows: When the first rotation angle in the angle information is 0 degrees, and the second rotation angle is a rotation angle in the (−)X-axis direction, the processor may classify the view as an AP CRANIAL view. When the first rotation angle in the angle information is in the (+)Y-axis direction and the second rotation angle is in the (−)X-axis direction, the processor may classify the view as an LAO CRANIAL view. When the first rotation angle in the angle information is in the (+)Y-axis direction and the second rotation angle is 0 degrees, the processor may classify the view as an LAO view. When the first rotation angle in the angle information is in the (−)Y-axis direction and the second rotation angle is 0 degrees, the processor may classify the view as an RAO view. For the left anterior descending artery, the processor may classify the view as follows: When both the first and second rotation angles in the angle information are 0 degrees, the processor may classify the view as an AP view. When the first rotation angle in the angle information is 0 degrees and the second rotation angle is in the (−)X-axis direction, the processor may classify the view as an AP CRANIAL view. When the first rotation angle in the angle information is in the (+)Y-axis direction and the second rotation angle is in the (−)X-axis direction, the processor may classify the view as an LAO CRANIAL view. When the first rotation angle in the angle information is in the (−)Y-axis direction and the second rotation angle is in the (−)X-axis direction, the processor may classify the view as an RAO CRANIAL view. For the left circumflex artery, the processor may classify the view as follows: When both the first and second rotation angles in the angle information are 0 degrees, the processor may classify the view as an AP view. When the first rotation angle in the angle information is 0 degrees and the second rotation angle is in the (+)X-axis direction, the processor may classify the view as an AP CAUDAL view. When the first rotation angle in the angle information is in the (−)Y-axis direction and the second rotation angle is in the (+)X-axis direction, the processor may classify the view as an RAO CAUDAL view. For the left main coronary artery, the processor may classify the view as follows: When the first rotation angle in the angle information is in the (+)Y-axis direction and the second rotation angle is in the (+)X-axis direction, the processor may classify the view as an LAO CAUDAL view.

The processor may then designate (or assign) the classified view information as a class along with the vessel type, as shown in Table 1. At this time, the processor may add a class to the class list to allow vessel classification for images other than CAG images among the cardiovascular images (e.g., the ("Non-CAG", " ") class in Table 1). Additionally, to handle cases where the imaging angle lies between a plurality of views, making it difficult to classify into any single view, the processor may add a dummy class containing only the vessel type without view information (e.g., the ("RCA", " ") class, ("LAD", " ") class, ("LCX", " ") class, and ("LM", " ") class in Table 1) to the class list.

TABLE 1

| Class | Identification number | Class | Identification number |
|---|---|---|---|
| ("Non-CAG", "") | −1 | ("LAD", "RAO CRANIAL") | 7 |
| ("RCA", "AP CRANIAL") | 0 | | |
| ("RCA", "LAO CRANIAL") | 1 | ("LAD", "") | 12 |
| ("RCA", "LAO") | 2 | ("LCX", "AP") | 4 |
| ("RCA", "RAO") | 3 | ("LCX", "AP CAUDAL") | 8 |
| ("RCA", "") | 11 | ("LCX", "RAO CAUDAL") | 9 |
| ("LAD", "AP") | 4 | ("LCX", "") | 13 |
| ("LAD", "AP CRANIAL") | 5 | ("LM", "LAO CAUDAL") | 10 |
| ("LAD", "LAO CRANIAL") | 6 | ("LM", "") | 14 |

In the following description, as shown in Table 1, view information designated as a class along with the vessel type may be referred to as a "valid view," while combinations of vessel types and view information that are assigned as dummy classes or not assigned as classes (e.g., the combination of RCA with AP view) may be referred to as "invalid views."

The processor may then train the machine learning model to classify views using images as input, based on the class information (e.g., class list). At this time, the processor may limit the types of primary vessels identifiable for each view and train the machine learning model to classify the primary vessels in the image accordingly. As the class information shown in Table 1, the processor may handle identification numbers of classes related to the AP view (e.g., the ("LAD", "AP") class and the ("LCX", "AP") class in Table 1) in the same manner. In this case, the processor may train the machine learning model so that the types of vessels identifiable in the AP view include at least one of the left anterior descending artery or the left circumflex artery. In some configurations, the processor may set different identification numbers for classes associated with the AP view (e.g., the ("LAD", "AP") and ("LCX", "AP") classes in Table 1). In this case, the processor may train the machine learning model so that the types of vessels identifiable in the AP view include either the left anterior descending artery or the left circumflex artery.

The processor may then input the image into the machine learning model in relation to the inference process preformed using the trained machine learning model. The processor may generate weights (e.g., Gaussian weights) based on the intensity of the contrast agent and using a predetermined number of points in the image, and based on the generated weights, at least one representative frame may be created (or extracted). Alternatively, the processor may generate weights based on a consistently predetermined number of points and create (or extract) at least one representative frame based on the generated weights. The processor may then input the at least one representative frame into the machine learning model.

The processor may then classify the view based on the inference result for at least one representative frame through the machine learning model. In this case, the processor may classify the view based on the class information. Additionally, the processor may restrict the types of vessels that may be identified in the image based on the classified view. The processor may then classify the vessels included in the image.

When the processor classifies the view based on the inference result for a plurality of representative frames through the machine learning model, the processor may determine the final result based on the class information. For example, the processor may determine the final result for the inference results of a plurality of representative frames through a voting method. To describe this in more detail, the processor may determine the combination of the type of vessel and the view information corresponding to the selected valid view as the final result if a valid view is selected as a result of the voting conducted on the inference results of the plurality of representative frames based on the class information. Alternatively, if an invalid view is selected as a result of the voting conducted on the inference results of the plurality of representative frames based on the class information, the processor may conduct a re-vote on the remaining view excluding the invalid view from the inference results of the plurality of representative frames. In this case, if a valid view is selected as a result of the re-vote, the processor may determine the combination of the type of vessel and the view information corresponding to the selected valid view as the final result. Alternatively, if all results are invalid views after the re-vote, the processor may conduct another vote based on a second confidence level (2nd confidence). Then, if a valid view is selected as a result of the second vote, the processor may determine the combination of the type of vessel and the view information corresponding to the selected valid view as the final result. Alternatively, if the result of the second vote is an invalid view or an image other than a CAG image (e.g., a non-CAG image), the processor may conduct a final vote based on the first confidence level only for the view information of the class that includes the type of vessel from the initial inference results, thereby determining the final result.

Figure 11:
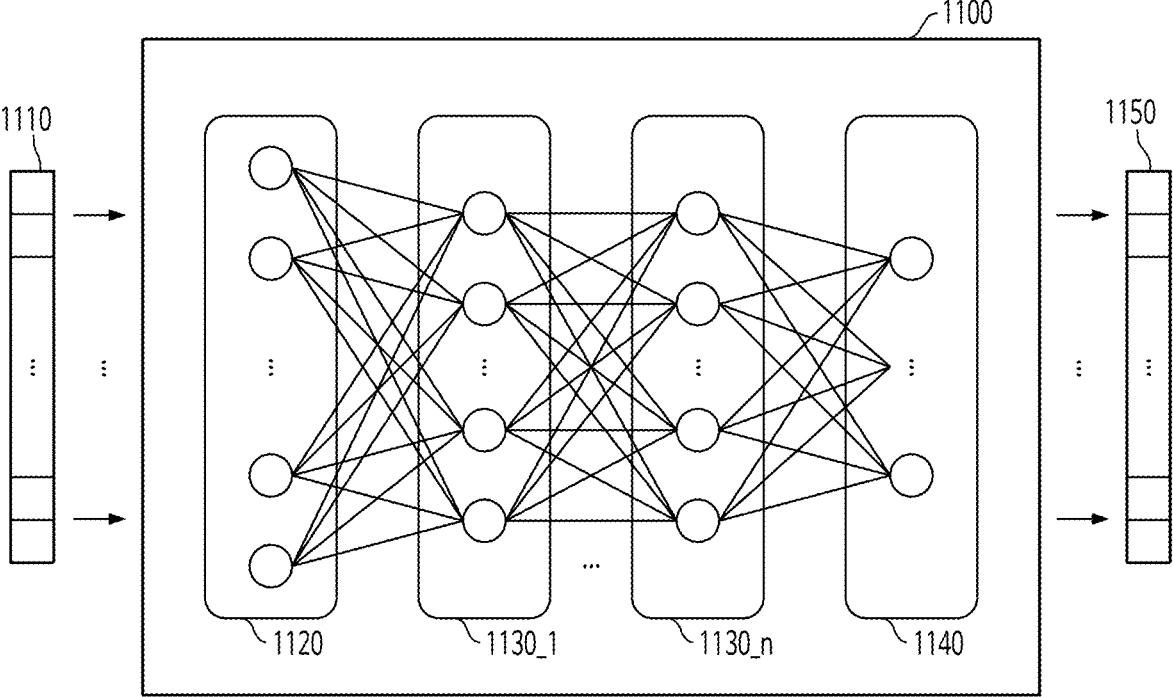
FIG. 11 is a diagram showing an artificial neural network model according to an example of the present disclosure.

FIG. 11 illustrates an artificial neural network model 1100 according to an example of the present disclosure. Referring to FIG. 11, the artificial neural network model 1100 is an example of a machine learning model and may represent a statistical learning algorithm or the architecture that executes this algorithm, which is implemented based on the architecture of biological neural networks in the field of machine learning technology and cognitive science.

The artificial neural network model 1100 may represent a machine learning model with problem solving capabilities by learning that nodes, which are artificial neurons that form a network by combining synapses like a biological neural network, repeatedly adjust the weights of synapses so that the error between the correct output corresponding to a specific input and the inferred output is reduced. For example, the artificial neural network model 1100 may include any probabilistic model, neural network model, or the like used in artificial intelligence learning methods such as machine learning and deep learning.

The vessel classification model as described above may be generated in the form of the artificial neural network model 1100. For example, the artificial neural network model 1100 may receive an image capturing the cardiovascular vessels of a subject and angle information of the image acquisition device relative to the subject and, based on theses, may estimate at least one type of cardiovascular vessel included in the image.

The artificial neural network model 1100 may be implemented as a multi-layer perceptron (MLP) composed of multiple layers of nodes and connections between them. The artificial neural network model 1100 may be implemented using one of the artificial neural network model architectures that include a multi-layer perceptron. The artificial neural network model 1100 may include an input layer 1120 that receives input data 1110 (or input signals) from an external source, an output layer 1140 that outputs output data 1150 (or output signals) corresponding to the input data 1110, and n hidden layers 1130_1 to 1130_n, where n is a positive integer, which are positioned between the input layer 1120 and the output layer 1140, receive signals from the input layer 1120, extract features, and transmit them to the output layer 1140. Here, the output layer 1140 may receive signals from the hidden layers 1130_1 to 1130_n and output them externally.

The learning methods of the artificial neural network model 1100 may include supervised learning, in which the model is trained to optimize problem-solving based on the input of correct teacher signals (or labels), and unsupervised learning, which does not require teacher signals. The electronic device (e.g., electronic device 100 in FIGS. 1 and 2) may train the artificial neural network model 1100 using an image capturing the cardiovascular vessels of a subject and angle information of the image acquisition device relative to the subject.

The electronic device may generate training data to train the artificial neural network model. For example, the electronic device may generate a training dataset that includes an image of the cardiovascular vessels of the subject and angle information of the image acquisition device relative to the subject. The electronic device may then train the artificial neural network model based on the generated training dataset to identify at least one type of cardiovascular vessel included in the image (or classify vessels in the image).

The input variables of the artificial neural network model 1100 may include an image of the cardiovascular vessels of the subject and angle information of the image acquisition device relative to the subject. When these input variables as described above are input through the input layer 1120, the output variables from the output layer 1140 of the artificial neural network model 1100 may include information identifying at least one type of cardiovascular vessel included in the image (or vessel classification information).

As described above, a plurality of output variables corresponding to a plurality of input variables are respectively matched to the input layer 1120 and the output layer 1140 of the artificial neural network model 1100, and the synaptic values between the nodes included in the input layer 1120, the hidden layers 1130_1 to 1130_n, and the output layer 1140 are adjusted, enabling the model to be trained so that correct outputs corresponding to specific inputs may be extracted. Through this learning process, the characteristics hidden within the input variables of the artificial neural network model 1100 may be identified, and the synaptic values (or weights) between the nodes of the artificial neural network model 1100 may be adjusted to reduce the error between the calculated output variables based on the input variables and the target outputs. In addition, the electronic device may train an algorithm that receives, as input, an image capturing the cardiovascular vessels of the subject and the angle information of the image acquisition device relative to the subject, and it may perform training in a manner that minimizes the loss with respect to the information identifying at least one type of cardiovascular vessel included in the image (or vessel classification information, i.e., annotation information). Using the artificial neural network model 1100 trained in this manner, information identifying at least one type of cardiovascular vessel included in the image may be estimated.

The flowchart and description above are merely examples and may be implemented differently in some examples. For example, in some examples, the order of respective steps may be changed, some steps may be repeatedly performed, some steps may be omitted, or some steps may be added.

The method described above may be provided as a computer program stored in a computer-readable recording medium for execution on a computer. The medium may be a type of medium that continuously stores a program executable by a computer, or temporarily stores the program for execution or download. In addition, the medium may be a variety of recording means or storage means having a single piece of hardware or a combination of several pieces of hardware, and is not limited to a medium that is directly connected to any computer system, and accordingly, may be present on a network in a distributed manner. An example of the medium includes a medium configured to store program instructions, including a magnetic medium such as a hard disk, a floppy disk, and a magnetic tape, an optical medium such as a CD-ROM and a DVD, a magnetic-optical medium such as a floptical disk, and a ROM, a RAM, a flash memory, etc. In addition, other examples of the medium may include an app store that distributes applications, a site that supplies or distributes various software, and a recording medium or a storage medium managed by a server.

The methods, operations, or techniques of the present disclosure may be implemented by various means. For example, these techniques may be implemented in hardware, firmware, software, or a combination thereof. Those skilled in the art will further appreciate that various illustrative logical blocks, modules, circuits, and algorithm steps described in connection with the disclosure herein may be implemented in electronic hardware, computer software, or combinations of both. To clearly illustrate this interchangeability of hardware and software, various illustrative components, blocks, modules, circuits, and steps have been described above generally in terms of their functionality. Whether such a function is implemented as hardware or software varies depending on design requirements imposed on the particular application and the overall system. Those skilled in the art may implement the described functions in varying ways for each particular application, but such implementation should not be interpreted as causing a departure from the scope of the present disclosure.

In a hardware implementation, processing units used to perform the techniques may be implemented in one or more ASICs, DSPs, digital signal processing devices (DSPDs), programmable logic devices (PLDs), field programmable gate arrays (FPGAs), processors, controllers, microcontrollers, microprocessors, electronic devices, other electronic units designed to perform the functions described in the present disclosure, computer, or a combination thereof.

Accordingly, various example logic blocks, modules, and circuits described in connection with the present disclosure may be implemented or performed with general purpose processors, DSPs, ASICs, FPGAs or other programmable logic devices, discrete gate or transistor logic, discrete hardware components, or any combination of those designed to perform the functions described herein. The general purpose processor may be a microprocessor, but in the alternative, the processor may be any related processor, controller, microcontroller, or state machine. The processor may also be implemented as a combination of computing devices, for example, a DSP and microprocessor, a plurality of microprocessors, one or more microprocessors associated with a DSP core, or any other combination of the configurations.

In the implementation using firmware and/or software, the techniques may be implemented with instructions stored on a computer-readable medium, such as random access memory (RAM), read-only memory (ROM), non-volatile random access memory (NVRAM), programmable read-only memory (PROM), erasable programmable read-only memory (EPROM), electrically erasable PROM (EE-PROM), flash memory, compact disc (CD), magnetic or optical data storage devices, etc. The instructions may be executable by one or more processors, and may cause the processor(s) to perform certain aspects of the functions described in the present disclosure.

When implemented in software, the techniques may be stored on a computer-readable medium as one or more instructions or codes, or may be transmitted through a computer-readable medium. The computer-readable media include both the computer storage media and the communication media including any medium that facilitates the transmission of a computer program from one place to another. The storage media may also be any available media that may be accessible to a computer. By way of non-limiting example, such a computer-readable medium may include RAM, ROM, EEPROM, CD-ROM or other optical disk storage, magnetic disk storage or other magnetic storage devices, or any other media that can be used to transmit or store desired program code in the form of instructions or data structures and can be accessible to a computer. In addition, any connection is properly referred to as a computer-readable medium.

For example, if the software is sent from a website, server, or other remote sources using coaxial cable, fiber optic cable, twisted pair, digital subscriber line (DSL), or wireless technologies such as infrared, wireless, and microwave, the coaxial cable, the fiber optic cable, the twisted pair, the digital subscriber line, or the wireless technologies such as infrared, wireless, and microwave are included within the definition of the medium. The disks and the discs used herein include CDs, laser disks, optical disks, digital versatile discs (DVDs), floppy disks, and Blu-ray disks, where disks usually magnetically reproduce data, while discs optically reproduce data using a laser. The combinations described above should also be included within the scope of the computer-readable media.

The software module may reside in RAM memory, flash memory, ROM memory, EPROM memory, EEPROM memory, registers, hard disk, removable disk, CD-ROM, or any other form of storage medium known. An exemplary storage medium may be connected to the processor such that the processor may read or write information from or to the storage medium. Alternatively, the storage medium may be integrated into the processor. The processor and the storage medium may exist in the ASIC. The ASIC may exist in the user terminal. Alternatively, the processor and storage medium may exist as separate components in the user terminal.

Although the examples described above have been described as utilizing aspects of the currently disclosed subject matter in one or more standalone computer systems, aspects are not limited thereto, and may be implemented in conjunction with any computing environment, such as a network or distributed computing environment. Furthermore, the aspects of the subject matter in the present disclosure may be implemented in multiple processing chips or apparatus, and storage may be similarly influenced across a plurality of apparatus. Such apparatus may include PCs, network servers, and portable apparatus.

Although the present disclosure has been described in connection with some examples herein, various modifications and changes can be made without departing from the scope of the present disclosure, which can be understood by those skilled in the art to which the present disclosure pertains. In addition, such modifications and changes should be considered within the scope of the claims appended herein.

What is claimed is:

1. A method performed by at least one processor, the method comprising:
   acquiring an image including cardiovascular vessels of a subject and angle information of an image acquisition device relative to the subject;
   identifying at least one type of a cardiovascular vessel included in the image by:
      providing, as input to a trained machine learning model, the image and the angle information; and
      receiving, as output from the trained machine learning model, output data indicating the at least one type of the cardiovascular vessel included in the image; and
   outputting a signal associated with the image, wherein the signal indicates the identified at least one type of the cardiovascular vessel;
   identifying one or more errors in the output data indicating the at least one type of the cardiovascular vessel included in the image; and
   correcting the one or more errors by further training the trained machine learning model,
   wherein the trained machine learning model is generated by training, using training data, an artificial neural network to receive an input image and input angle information and output an identification of one or more types of cardiovascular vessels depicted in the input image, wherein training the artificial neural network comprises modifying one or more weights of one or more nodes of the artificial neural network based on the training data, and
   wherein the training data comprises:
      a plurality of images of one or more cardiovascular vessels at a variety of different angles;
      information indicating, for each of the plurality of images, one or more angles; and
      tagging information indicating, for each cardiovascular vessel of the one or more cardiovascular vessels, a type of the cardiovascular vessel.

2. The method of claim 1, wherein the angle information comprises:
   first rotation angle information of the image acquisition device corresponding to a first rotation angle around a first axis of a vertical direction of the subject, and
   second rotation angle information of the image acquisition device corresponding to a second rotation angle around a second axis of a horizontal direction of the subject.

3. The method of claim 1, wherein the plurality of images of the one or more cardiovascular vessels at the variety of different angles correspond to a plurality of predetermined angles relative to a human body, and wherein the angle information provided as input to the trained machine learning model indicates an angle other than the plurality of predetermined angles.

4. The method of claim 1, wherein the output from the trained machine learning model identifies two or more cardiovascular vessels included in the image.

5. The method of claim 1, further comprising:

correcting, based on the angle information of the image acquisition device relative to the subject, the identified at least one type of the cardiovascular vessel to another type.

6. The method of claim 1, wherein the output data indicating the at least one type of the cardiovascular vessel included in the image further comprises:

an indication of a view corresponding to the acquired image.

7. The method of claim 1, wherein the training data further comprises:

non-coronary angiography (non-CAG) images.

8. The method of claim 1, wherein the identifying the at least one type of the cardiovascular vessel further comprises:

limiting, based on the image, types of cardiovascular vessels that can be identified in the acquired image.

9. The method of claim 1, wherein the providing, as input to the trained machine learning model, the image and the angle information comprises:

extracting, based on weight values associated with a number of points in the image, at least one representative frame from the image; and providing, as the input to the trained machine learning model, the at least one representative frame.

10. The method of claim 9, wherein the extracting the at least one representative frame comprises:

based on the at least one representative frame including a plurality of representative frames, determining a final result through a machine-voting method based on inference results of the plurality of representative frames by the trained machine learning model.

11. An electronic device comprising:

at least one processor; and a memory storing computer-readable instructions that, when executed by the at least one processor, are configured to cause the electronic device to:

acquire an image including cardiovascular vessels of a subject and angle information of an image acquisition device for the subject;

identify at least one type of a cardiovascular vessel included in the image by:

providing, as input to a trained machine learning model, the image and the angle information; and receiving, as output from the trained machine learning model, output data indicating the at least one type of the cardiovascular vessel included in the image;

output a signal associated with the image, wherein the signal indicates the identified at least one type of the cardiovascular vessel;

identify one or more errors in the output data indicating the at least one type of the cardiovascular vessel included in the image; and correct the one or more errors by further training the trained machine learning model, wherein the trained machine learning model is generated by training, using training data, an artificial neural network to receive an input image and input angle information and output an identification of one or more types of cardiovascular vessels depicted in the input image, wherein training the artificial neural network comprises modifying one or more weights of one or more nodes of the artificial neural network based on the training data, and wherein the training data comprises:

a plurality of images of one or more cardiovascular vessels at a variety of different angles;

information indicating, for each of the plurality of images, one or more angles; and tagging information indicating, for each cardiovascular vessel of the one or more cardiovascular vessels, a type of the cardiovascular vessel.

12. The electronic device of claim 11, further comprising:

a main body comprising an elevating driver;

an elevating part fixed to a top portion of the elevating driver and configured to elevate in a first direction;

a rotating part having a first end rotatably connected to the elevating part around a first axis in a second direction perpendicular to the first direction and having a curved surface formed at a second end of the rotating part;

a C-shaped frame part slidably connected to the curved surface and configured in a C shape;

an X-ray generating device disposed at a first end of the C-shaped frame part; and the image acquisition device disposed at a second end of the C-shaped frame part.

13. The electronic device of claim 12, wherein the angle information comprises:

first rotation angle information of the image acquisition device formed when the rotation part rotates around the first axis; and second rotation angle information of the image acquisition device formed when the C-shaped frame part slides and centered around a second axis in a third direction perpendicular to the first and second directions.

14. A non-transitory computer-readable storage medium storing computer-readable instructions that, when executed by at least one processor, cause the at least one processor to:

acquire an image including cardiovascular vessels of a subject and angle information of an image acquisition device for the subject;

identify at least one type of a cardiovascular vessel included in the image by:

providing, as input to a trained machine learning model, the image and the angle information; and receiving, as output from the trained machine learning model, output data indicating the at least one type of the cardiovascular vessel included in the image; and output a signal associated with the image, wherein the signal indicates the identified at least one type of the cardiovascular vessel;

identify one or more errors in the output data indicating the at least one type of the cardiovascular vessel included in the image; and correct the one or more errors by further training the trained machine learning model, wherein the trained machine learning model is generated by training, using training data, an artificial neural network to receive an input image and input angle information and output an identification of one or more types of cardiovascular vessels depicted in the input image, wherein training the artificial neural network comprises modifying one or more weights of one or more nodes of the artificial neural network based on the training data, and wherein the training data comprises:

a plurality of images of one or more cardiovascular vessels at a variety of different angles;

information indicating, for each of the plurality of images, one or more angles; and tagging information indicating, for each cardiovascular vessel of the one or more cardiovascular vessels, a type of the cardiovascular vessel.

15. The non-transitory computer-readable storage medium of claim 14, wherein the angle information comprises:

first rotation angle information of the image acquisition device corresponding to a first rotation angle around a first axis of a vertical direction of the subject, and second rotation angle information of the image acquisition device corresponding to a second rotation angle around a second axis of a horizontal direction of the subject.

16. The non-transitory computer-readable storage medium of claim 14, wherein the plurality of images of the one or more cardiovascular vessels at the variety of different angles correspond to a plurality of predetermined angles relative to a human body, and wherein the angle information provided as input to the trained machine learning model indicates an angle other than the plurality of predetermined angles.

17. The method of claim 10, wherein the determining the final result comprises:

based on a first valid view being selected based on a machine-voting result of inference results of the plurality of representative frames, determining, as the final result, a class including a type of vessel and view information corresponding to the selected first valid view.

18. The method of claim 10, wherein the determining the final result comprises:

based on a first invalid view being selected based on a machine-voting result of inference results of the plurality of representative frames, re-voting on the remaining inference results excluding the first invalid view from the inference results of the plurality of representative frames, and based on a second valid view being selected based on a re-voting result, determining, as the final result, a class including a type of vessel and view information corresponding to the selected second valid view;

based on a second invalid view being selected based on a machine-voting result of the inference results of the plurality of representative frames, re-voting on the remaining inference results excluding the second invalid view from the inference results of the plurality of representative frames, and based on all results corresponding to invalid views after re-voting, re-voting with a second confidence, and based on a third valid view being selected based on a re-voting result associated with the second confidence, determining, as the final result, a class including a type of vessel and view information corresponding to the selected third valid view; or based on a third invalid view being selected based on a machine-voting result of the inference results of the plurality of representative frames, re-voting on the remaining inference results excluding the third invalid view from the inference results of the plurality of representative frames, and based on all results corresponding to invalid views after re-voting, re-voting with a second confidence, and based on an invalid view or a non-coronary angiography (non-CAG) image being selected after re-voting with the second confidence, re-voting with a first confidence only on view information of a class including a type of vessel from an initial inference result to determine the final result.

* * * * *